(12) United States Patent
Erickson et al.

(10) Patent No.: US 6,254,008 B1
(45) Date of Patent: Jul. 3, 2001

(54) BOARD MOUNTED SENSOR PLACEMENT INTO A FURNACE DUCT

(75) Inventors: James E. Erickson, Eagan; Thomas C. Tinucci, Eden Prairie, both of MN (US)

(73) Assignee: Honeywell International, Inc., Morristown, NJ (US)

( * ) Notice: Subject to any disclaimer, the term of this patent is extended or adjusted under 35 U.S.C. 154(b) by 0 days.

(21) Appl. No.: 09/312,408

(22) Filed: May 14, 1999

(51) Int. Cl.[7] ............................... B01F 3/02; G01D 11/24
(52) U.S. Cl. ..................... 236/44 A; 73/431; 126/113; 374/146
(58) Field of Search ................. 236/DIG. 19, 44 R, 236/44 A; 126/113; 73/431, 29.02; 374/147

(56) References Cited

U.S. PATENT DOCUMENTS

| | | | |
|---|---|---|---|
| 1,418,913 | * 6/1922 | Gold | 236/DIG. 19 |
| 3,523,217 | 8/1970 | Stiles | 317/120 |
| 4,198,279 | 4/1980 | Brown et al. | 204/195 S |
| 4,706,808 | 11/1987 | Guetersloh | 206/305 |
| 5,252,260 | 10/1993 | Schuman | 261/26 |
| 5,351,035 | 9/1994 | Chrisco | 240/626 |
| 5,396,796 | * 3/1995 | Kotani et al. | 73/431 |

OTHER PUBLICATIONS

Aprilaire Auto–Trac™ Control System, Model #56, Operating Instructions, Research Products Corporation (1996).

* cited by examiner

Primary Examiner—William Wayner
(74) Attorney, Agent, or Firm—Charles L. Rubow

(57) ABSTRACT

A method and apparatus for protecting humidity sensing equipment within an enclosure that can be mounted in the return airflow of a furnace duct. The humidity sensing equipment is mounted on a printed wiring board, which is protected between a mounting base and an operational cover. The mounting base includes a protective shield which allows the humidity sensing equipment to protrude into the furnace duct and prevents damage to the humidity sensing equipment during installation.

29 Claims, 4 Drawing Sheets

BOARD MOUNTED SENSOR PLACEMENT INTO A FURNACE DUCT

CROSS-REFERENCE TO RELATED APPLICATIONS

Not Applicable.

STATEMENT REGARDING FEDERALLY SPONSORED RESEARCH OR DEVELOPMENT

Not Applicable.

REFERENCE TO A "MICROFICHE APPENDIX"

Not Applicable.

BACKGROUND OF THE INVENTION

This invention relates generally to the field of humidity control devices, and more specifically to humidistat controllers having a humidity sensor mounted into a furnace duct.

In the past, a common approach to humidity control within residential and commercial buildings has been to install a humidistat to sense and control the ambient humidity within an enclosed space. These humidistats were commonly designed to sense the temperature and/or relative humidity within the enclosed space and then provide control to a usually remote device, which would operate to humidify or dehumidify the room air. Traditionally, these humidistats were mounted either on a wall in a common living area, or on a furnace duct or plenum.

Although a conventional wall mounted humidistat is readily accessible to the occupants for proper adjustment of the humidity level, it often results in significant installation problems due to the type of wall construction. Additionally, since the humidistat is commonly configured to monitor temperature and relative humidity, there may be instances where the sensed humidity may not be an accurate representation of the humidity throughout the building. This may then result in an improper adjustment of the humidity level.

Placement of the humidistat on the duct or plenum of a furnace has the initial advantage of allowing the humidity-sensing element to be in contact with the return air from the building. This allows humidity or temperature sensing elements within the humidistat to obtain an average relative humidity and temperature of the entire living space. Likewise, placement near the furnace typically involves shorter cable runs to any associated humidity controlling equipment, saving additional installation costs.

Prior commercial humidistats have generally included at least a relative humidity sensing element adapted to be partially enclosed within a housing, the housing including a wall or furnace-mountable base and front cover attached to the base. The bases of the prior commercial devices were generally planar and required a large rectangular cutout in the furnace duct to expose the sensing element to the return air. The humidity sensing element was often mounted to the front face of the housing, and a cover was attachable to the base via forwardly extending spring clips on the base ends, which latched over projections formed on the cover ends. One example of this type of humidistat may be found in U.S. Pat. No. 3,523,217.

Humidistats which are designed to place the humidity-sensing element within the return air furnace duct, unfortunately have a significant drawback. Due to the size and nature of the humidity control, large rectangular holes were required to be cut into the furnace duct or plenum to allow exposure of the humidity-sensing element to the duct airflow. These holes ranged in size, but were often two inches by four inches, which required the cutting to be performed with common sheet metal cutting tools. In a typical installation, the installer would create a hole in the ductwork (usually by means of a drill), and then further expand the hole to the correct size with sheet metal cutting snips. Furthermore, due to the large hole placed into the duct or plenum, building inspectors often require leaks around these rectangular cutouts to be sealed by caulking.

The Applicant's invention now described provides an improved humidistat mounting method and apparatus which allows sensor placement within a furnace duct with minimal damage to the duct.

BRIEF SUMMARY OF THE INVENTION

The present invention is a method and apparatus for protecting humidity sensing equipment within an enclosure that can be mounted in the return airflow of a furnace duct. In the method, a printed wiring board is first separated into two sections, which are and electrically connected via a flexible jumper. The flexible jumper is then bent so as to position the sections in distinct planes, one of the sections being inserted into a protective housing. The other of the sections carries a sensor, which is operable to sense one or more conditions and relay this information to associated controlling equipment located on the second printed wiring board.

Once the flexible jumpers are bent, the printed wiring boards may be inserted into a humidistat housing, and the sensing equipment extends though an opening in a mounting base. The sensing equipment is protected during installation by a protective shield, which is secured to the mounting base surrounding the sensing equipment. A cover may then be attached to the mounting base and the device may be secured to a furnace duct or plenum. Once secured, the sensing equipment extends into an opening cut into the furnace duct and is operable to obtain information regarding the air within the duct.

The apparatus of Applicant's invention follows closely the method described above.

DETAILED DESCRIPTION OF THE INVENTION

Figure 1:
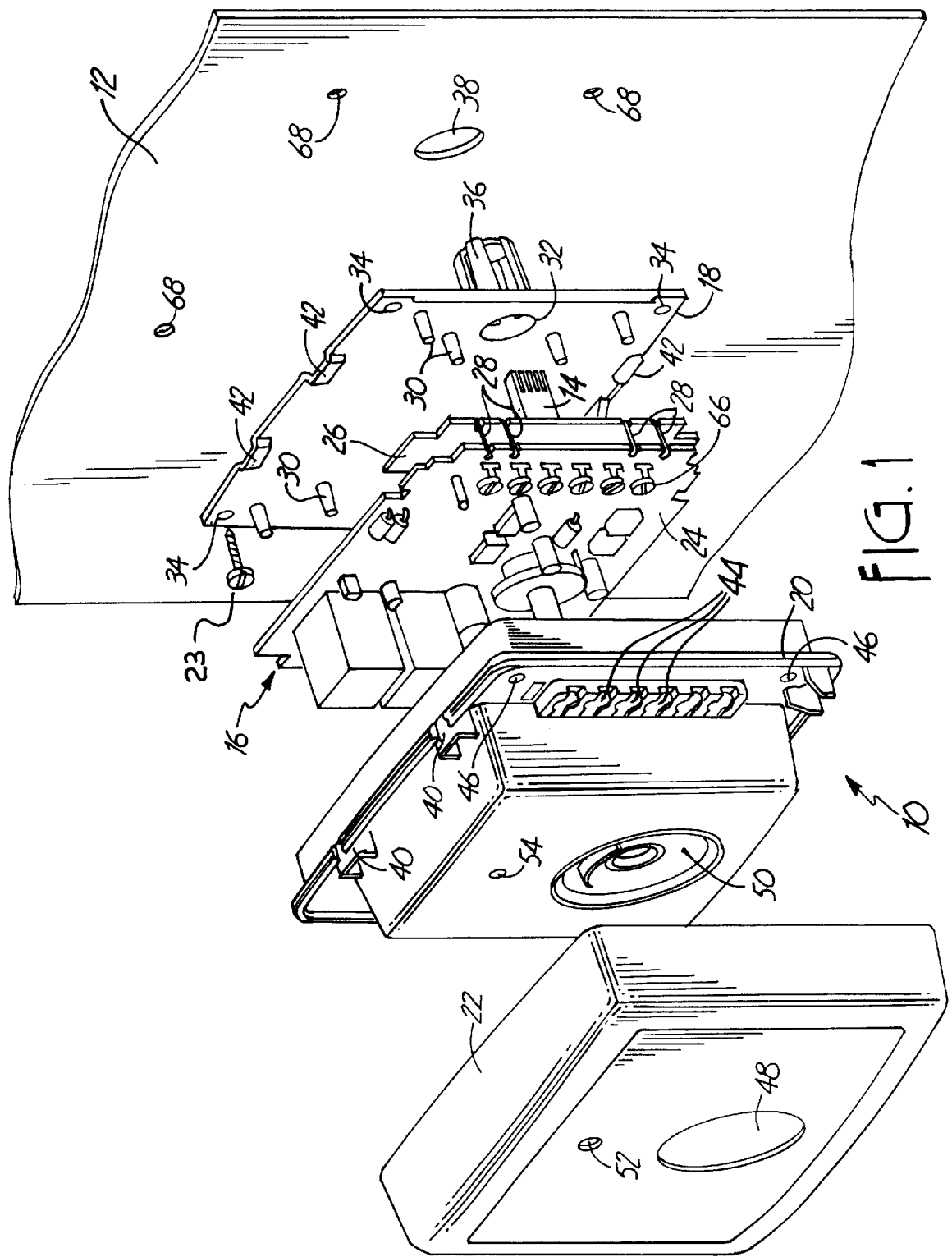
FIG. 1 is an exploded view of the humidistat of the present invention.

FIG. 1 shows an exploded view of the humidistat mounting method and apparatus of the present invention. The respective parts are shown as may be assembled to a furnace duct or plenum 12. The duct mounted humidistat 10, having sensing elements 14 secured on printed wiring board assembly 16, a mounting base plate 18, an operational cover 20, and a front cover 22 may be secured to duct 12 by means of self-tapping screws 23, or the like, via mounting holes 68.

The sensing elements 14 are disposed upon a U-shaped printed wiring board assembly 16, having two separate printed wiring boards 24 and 26, connected by electrical jumpers 28. The printed wiring board assembly 16 may initially be assembled in a planar position, as will be explained further in FIG. 2, and then bent into a U-shape before assembly onto the mounting base plate 18. This approach allows for a cost-effective assembly process since all components may be inserted via machine onto a single-sided printed wiring board array from the same direction.

The mounting base plate 18 includes several outwardly projecting bosses 30, an aperture 32, mounting holes 34, and a inwardly projecting protective shield 36. As shown in FIG. 1, when the device is assembled, printed wiring board assembly 16 is adjacent the mounting base plate 18, and prevented from further movement toward the mounting base plate 18 by the outwardly projecting bosses 30. Mounting holes 34 are provided to receive screws 23 that may be used to mount and secure the unit on the furnace duct 12. The aperture 32, when the mounting base plate 18 is assembled with the printed wiring board assembly 16, aligns with the inwardly projection of the sensing elements 14, and allows the sensing elements 14 to extend beyond the mounting base plate into duct 12 via hole 38. Similarly, when the mounting base plate 18 is mounted and secured to duct 12, the outwardly projecting protective shield 36 extends into hole 38 to prevent damage to the sensing elements 14 while the humidistat 10 is being handled during installation. Hole 38 may be sized so as to be slightly larger than the inwardly projecting protective shield 36. In the preferred embodiment, hole 38 is only ¾ inches in diameter, and may be drilled with a mechanical drill or the like. The outwardly projecting protective shield 36 extends entirely into hole 38 so that the humidistat 10 may be mounted flatly against the level surface of duct 12, minimizing any need for the sealing of leaks around the opening in the furnace duct.

The mounting base plate 18 is connected to the operational cover 20 by outwardly extending spring clips 40 on the operational cover ends, which latch over projections 42 formed on the mounting base plate ends. The operational cover 20 also contains several apertures 44 which allow screws 66 that are threadably engaged to the printed wiring board assembly 16, to project outwardly though the operational cover 20. The heads of the screws are received through the operational cover 20 so that wires or jumpers necessary for operation may be connected to the components on the printed wiring board assembly 16. Mounting holes, generally identified by reference numeral 46 on operational cover 20, align with the mounting holes 34 on the mounting base plate 18 when the humidistat is fully assembled. This allows the insertion of screws (not shown) as previous mentioned to secure the humidistat to the duct 12 though mounting holes 68.

Front cover 22, containing a large aperture 48 may secured to the operational cover 20 so as to protect any wire connections to screw terminals 66, and to cover any unsightly mounting screws. When assembled, aperture 48 aligns with a knob receptacle 50 to allow an adjustment knob (not shown) to extend through the front cover 22. Likewise, a smaller aperture 52 aligns with a status indicator 54 on the operational cover 20 when the front cover 22 is fully assembled. This allows the status indicator 54 to be observed even with the front cover 22 fully attached.

Figure 2A:
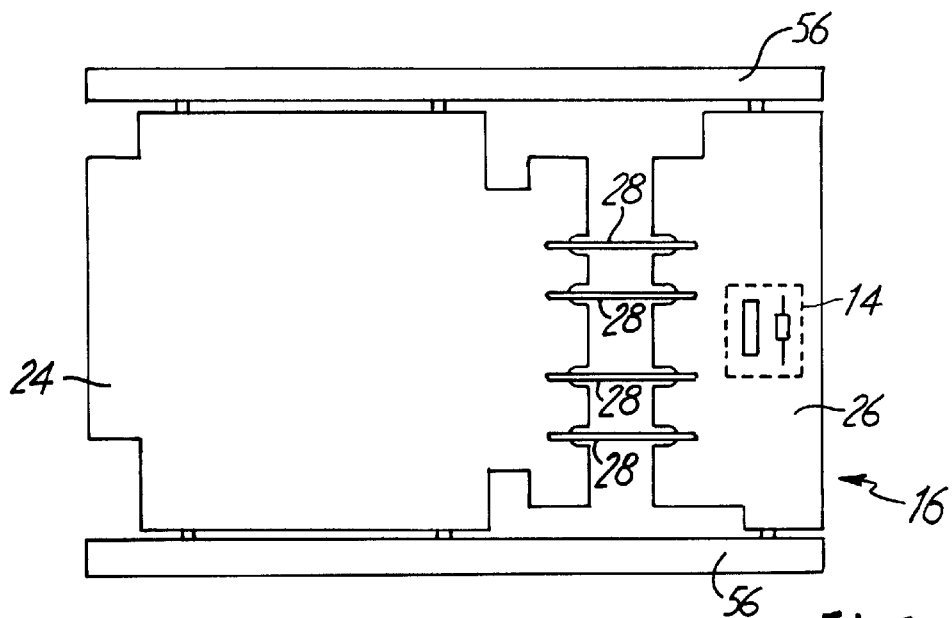
FIG. 2A depicts the manufacturing process of the printed wiring board of the present invention.

Referring now to FIG. 2A, the printed wiring board assembly 16 is shown in an unassembled state. Printed circuit boards 24 and 26 are initially secured to temporary rails 56 to be held in a single plane. This allows for simple insertion of the humidistat components onto one side of the printed wiring board assembly 16, including the sensing elements 14 on printed wiring board 26. Flexible jumpers 28 are also electrically secured between the printed wiring boards at the same time the boards are populated with components. Once the components are fully assembled onto the printed wiring board assembly 16, the temporary rails 56 are removed and printed wiring board 26 is folded toward printed wiring board 24.

Figure 2B:
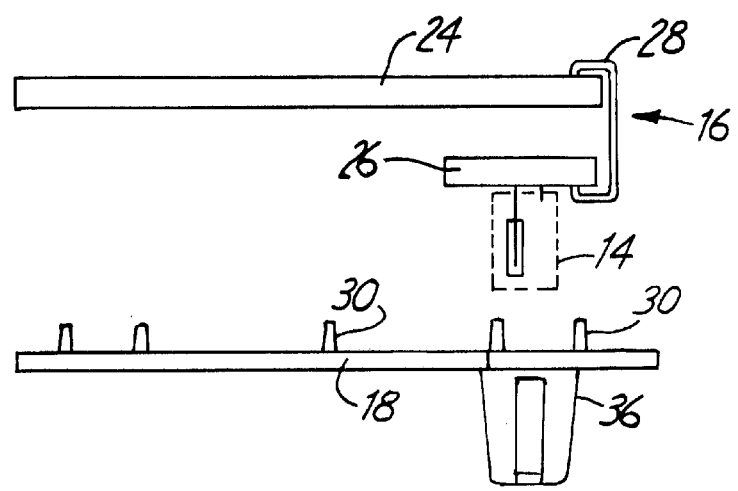
FIG. 2B depicts the assembly of the printed wiring board into the base of the humidistat.

FIG. 2B depicts the orientation of the printed wiring board assembly 16 as it is being assembled into the mounting base plate 18. Flexible jumpers 28 connect the two separate printed wiring boards 24 and 26, allowing the sensing elements 14 to be oriented 180 degrees from the components on the front of printed wiring board 24, once the humidistat is fully assembled. As explained in FIG. 1, the sensing elements 14 are inserted though the mounting base plate 18 and encased by the protective shield 36. Bosses 30 extend toward the printed wiring board assembly 16 to prevent movement and damage to the printed wiring board assembly 16 during operation. This allows installers to apply pressure to the screws 66 on the printed wiring board 24 through apertures 44 without flexing the printed wiring board 24. In the preferred embodiment, the protective shield 36 will operate to protect the fragile sensing elements 14 while still allowing adequate airflow to the sensing elements 14 to ensure normal humidistat operation.

Figure 3:
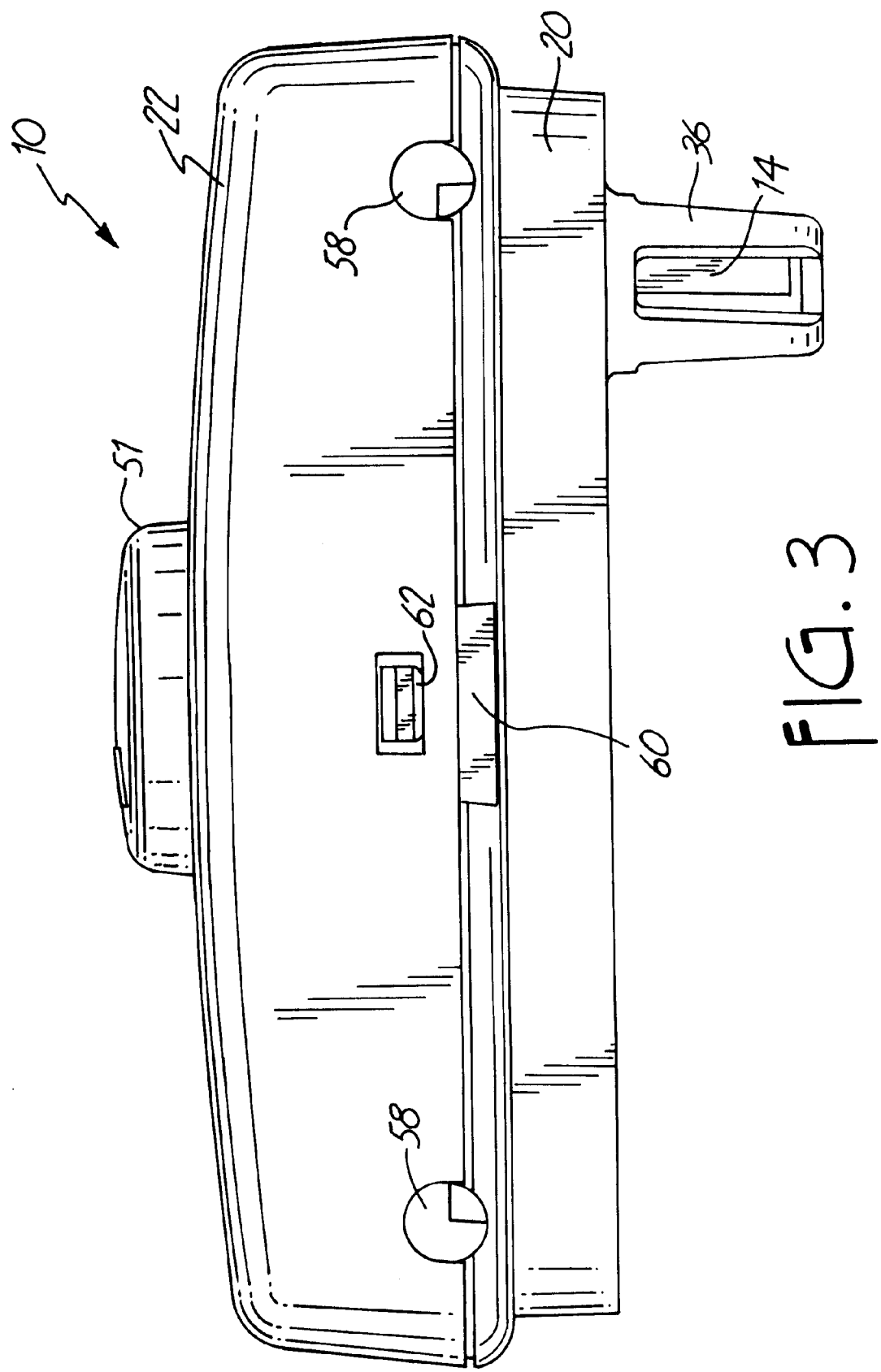
FIG. 3 depicts the humidistat of the present invention in an assembled state.

Referring now to FIG. 3, the respective parts are shown in an assembled state as protected by the front cover 22. Apertures 58 provide opening through which electrical cables (not shown) connecting the printed wiring board assembly 16 to a humidifier or dehumidifier may conveniently pass without interfering with ready assemblage of the humidistat 10. Also shown in FIG. 3 are the extending spring clips 60 on the operational cover 20, which latch over projections 62 formed on the front cover sides.

Figure 4:
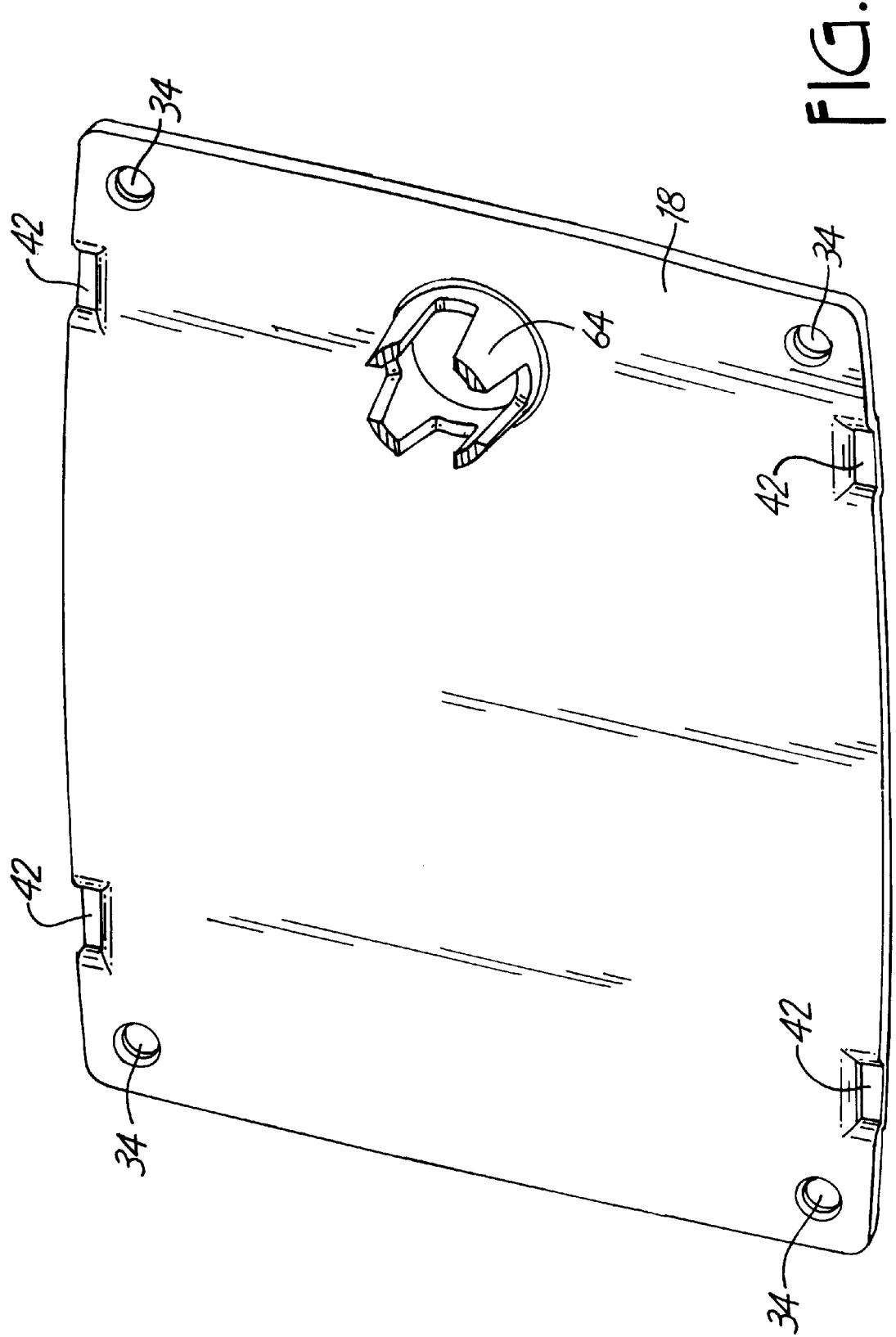
FIG. 4 depicts an alternate embodiment for the base of the present invention.

FIG. 4 depicts an alternative embodiment of the mounting base plate previously shown and described in FIG. 1. To increase the airflow to the sensing elements disposed within protective shield 64, the rear protective cover may be excluded. This results in a protective enclosure as formed by the remaining four extruding housing shield members.

In accordance with the foregoing description, the Applicants have provided a unique method and apparatus for protecting humidity sensing equipment within an enclosure that can be mounted in the return airflow of a furnace duct. Although a particular embodiment has been shown and described in illustrative purposes, other implementations which do not depart from the applicant's teachings will be apparent to those of ordinary skill in the relevant arts. It is intended that protection not be limited to a disclosed embodiment, but only by the terms of the following claims.

The embodiments of the invention in which an exclusive property right is claimed are defined as follows:

1. A method for mounting a humidity sensor in a furnace duct, comprising:
  a.) forming a base having an opening extending therethrough, said opening protected on one side by a protective shield;
  b.) separating a wiring board into first and second pieces, the first piece of said wiring board having a sensing element thereon and the second piece of said wiring board have associated controls thereon;
  c.) connecting the first and second pieces of said wiring board by means of a flexible jumper;
  d.) bending the flexible jumper so as to cause the first piece of said wiring board to lie essentially parallel to the second piece of said wiring board;
  e.) disposing said sensing element though the opening into the protective shield on said base; and
  f.) securing said base to the furnace duct so that the sensing element is placed into airflow within the furnace duct.

2. The method for mounting a humidity sensor of claim 1 further comprising the step of:
  $e_2$.) creating an opening in the furnace duct, the opening being large enough to permit passage of the protective shield therethrough.

3. The method for mounting a humidity sensor of claim 1 further comprising the steps of:
   h.) placing a first cover over said first and second wiring boards; and
   i.) fastening said first cover to said base.

4. The method for mounting a humidity sensor of claim 3 further comprising the steps of:
   j.) placing a second cover over said first cover; and
   k.) fastening said second cover to said first cover.

5. The method for mounting a humidity sensor of claim 1 wherein: said sensing element is a humidity-sensing element.

6. A humidistat mounting package for a printed circuit board, the printed circuit board having a sensor attached thereto, comprising:
   a longitudinally extending housing base having an opening for passthrough of the sensor, the opening covered by a generally perpendicular cylindrical frame surrounding the opening and defining a protective area surrounding the sensor;
   a housing cover;
   a attachment means for securing the first housing cover to the housing base; and
   a second attachment means for attaching the humidistat to a vertical surface.

7. The humidistat mounting package of claim 6 wherein said sensor is a humidity sensor.

8. The humidistat mounting package of claim 6 wherein said attachment means further comprises:
   at least one springable latching element secured to the housing cover; the at least one springable latching element operable to secure the cover to the base when the cover is pressed toward the base.

9. An improved humidity control mounting package of the type in which a sensing element is mounted proximate to a flat base plate and housing cover, the housing cover having a cooperative means for joining the cover to the base plate, wherein the improvement comprises:
   an opening in the base plate extending therethrough; and
   a protective shield disposed about the opening in the base plate, the protective shield extending outward from the base plate and the sensing element disposed within the protective shield.

10. The improved humidity control mounting package of claim 9 wherein the base plate is mountable to a furnace duct.

11. A base member for mounting a humidity control device comprising:
   a substantially flat plate having a plurality of mounting holes for securing said flat plate to a furnace plenum;
   an aperture extending though said flat plate, said aperture suitable for receiving a humidity sensing assembly;
   a protective shield disposed about said aperture, said protective shield extending away from the base plate and having openings for the passage of air; and
   a plurality of bosses extending from said flat plate.

12. The base member of claim 11 further including:
   at least one latching area, suitable for securing a springable latching element to the base plate.

13. A method for fabricating a device including a transducer for converting a sensed value of an environmental condition to an electrical variable and a board mounted circuit for processing the electrical variable, comprising the steps of:
   forming a circuit board having a primary surface and including first and second sections joined by at least one flexible jumper, the first section of the circuit board being adapted to hold on its primary surface and in electrical communication with said flexible jumper, a transducer for sensing a predetermined environmental condition, the second section of the circuit board having an electrical circuit substantially only on the primary surface thereof;
   folding the circuit board so that the primary surfaces of the first and second sections thereof are substantially non-coplaner;
   forming a base plate having an opening therethrough for allowing the transducer to be positioned for exposure to an environment of which the predetermined environmental condition is to be sensed;
   mounting the circuit board relative to the base plate so that the second section of the circuit board is adapted to position the transducer for exposure to said environment through the opening in the base plate.

14. The method of claim 13 wherein the step of folding the circuit board comprises folding the second section of said board substantially 180° relative to the first section thereof so that the primary surfaces of the first and second sections of said board face outwardly from one another.

15. The method of claim 14 wherein:
   the steps of forming the circuit board and securing the circuit board to the base plate are effective to position the transducer so that it extends through the opening in the base plate; and
   the step of forming the base plate includes forming a protective shield, having an inside and an outside, around the opening on a side of the base plate opposite that on which a cover assembly is to be mounted to form a protected region around the sensor location.

16. The method of claim 15 wherein the protective shield is in the form of a hollow projection extending from the base plate, and having at least one opening between the inside and outside thereof.

17. The method of claim 16:
   wherein the step of forming the circuit board comprises forming a circuit having at least one user adjustable component on the primary surface of the second section of the circuit board; and
   including the further step of securing a cover assembly to the base plate to enclose the circuit board, the cover assembly having an aperture therein through which the user adjustable component is accessible.

18. The method of claim 17 wherein:
   the transducer is a humidity sensor;
   the electrical circuit on the second section of the circuit board is adapted to provide an output signal determined, in part, by a humidity value sensed by the humidity sensor; and
   the user adjustable component of the electrical circuit is effective to input a humidity set point which, in part, determines the output signal of said circuit.

19. The method of claim 18 wherein:
   the circuit board is formed with at least one signal terminal thereon; and
   the cover assembly includes a first cover having a first opening therethrough through which the user adjustable component is accessible and having at least a second opening therethrough through which the signal terminal is accessible, the cover assembly further including a second cover having an opening therethrough through which the user adjustable component is accessible.

20. In a humidistat of the type having a humidity sensor located for exposure to air on one side of a barrier, the humidity sensor being mounted on a circuit board carrying circuitry for producing an output signal dependent on the humidity value sensed by the humidity sensor and on a humidity set point determined by a user set point control accessible from the side of the barrier opposite the location of the humidity sensor, the improvement which comprises:

a base plate having first and second oppositely facing principal surfaces and an opening therethrough;

a hollow protective shield, having an inside and outside, surrounding the opening through said base plate projecting from the first principal surface thereof, said hollow protective shield having at least one opening between the inside and outside thereof; and a printed circuit board having a primary surface and including first and second sections joined by at least one flexible jumper, the first section holding a humidity sensor in electrical communication with the flexible jumper, the second section of the printed circuit board carrying a circuit for receiving a signal communicated from the humidity sensor through the flexible jumper, the first section of the printed circuit board being folded so the primary surfaces of the first and second sections thereof are substantially non-coplaner, said printed circuit board being mounted so that the first section thereof is positioned proximate the second principal surface of said base plate and so that the humidity sensor is positioned on the base plate within said protective shield.

21. The apparatus of claim 20 wherein:

the first section of the printed circuit board is folded substantially 180° relative to the second section thereof so that the primary surfaces of the first and second sections of said printed circuit board face outwardly from one another.

22. An apparatus for converting a sensed value of an environmental condition to an electrical variable, comprising:

a circuit board having a primary surface, comprising:
  a transducer disposed on the primary surface of said circuit board for sensing a predetermined environmental condition;
  an electrical circuit disposed substantially on the primary surface of said circuit board, the circuit in electrical communication with the transducer;

a base plate having first and second oppositely facing principal surfaces and an opening therethrough, said circuit board positioned relative to said base plate so that the transducer is positioned for exposure to said environment through the opening in said base plate.

23. The apparatus of claim 22 wherein:

said circuit board comprises first and second sections joined by at least one flexible jumper, the first section of the circuit board being adapted to hold the transducer in electrical communication with said flexible jumper, the second section of the circuit board carrying the electrical circuit.

24. The apparatus of claim 23 wherein:

said circuit board is folded so that the primary surfaces of the first and second sections thereof are substantially non-coplanar.

25. The apparatus of claim 24 wherein:

said circuit board is folded substantially 180° relative to the first section thereof so that the principal surfaces of the first and second sections of said circuit board face outwardly from one another.

26. The apparatus of claim 22 further comprising:

a protective shield, having an inside and an outside, in the form of a hollow projection extending from said base plate to form a protected region around the opening, and having at least one opening between the inside and outside thereof.

27. The apparatus of claim 22 further comprising:

a user adjustable component on the primary surface of the circuit board; and a cover assembly secured to said base plate to enclose the circuit board, the cover assembly having an aperture therein through which the user adjustable component is accessible.

28. The apparatus of claim 27 wherein:

said circuit board further comprises at least one signal terminal; and said cover assembly includes a first cover having a first opening therethrough through which the user adjustable component is accessible and having at least a second opening therethrough through which the signal terminal is accessible, the cover assembly further including a second cover having an opening therethrough through which the user adjustable component is accessible.

29. The apparatus of claim 22 wherein:

the transducer is a humidity sensor; and the electrical circuit on said circuit board is adapted to provide an output signal determined, in part, by a humidity value sensed by the humidity sensor.

* * * * *